US009150515B2

United States Patent
Kuehl

(10) Patent No.: US 9,150,515 B2
(45) Date of Patent: Oct. 6, 2015

(54) IMIDAZOLIUM SALTS AND CARBENE METAL COMPLEXES BASED THEREON FOR USE AS BIOANALYTICAL MARKERS FOR BIOMOLECULES

(75) Inventor: Olaf Kuehl, Greifswald (DE)

(73) Assignee: ERNST-MORITZ-ARNDT-UNIVERSITÄT GREIFSWALD, Greifswald (DE)

( * ) Notice: Subject to any disclaimer, the term of this patent is extended or adjusted under 35 U.S.C. 154(b) by 0 days.

(21) Appl. No.: 13/821,941

(22) PCT Filed: Sep. 5, 2011

(86) PCT No.: PCT/EP2011/065266
§ 371 (c)(1),
(2), (4) Date: Mar. 8, 2013

(87) PCT Pub. No.: WO2012/034880
PCT Pub. Date: Mar. 22, 2012

(65) Prior Publication Data
US 2013/0171071 A1 Jul. 4, 2013

(30) Foreign Application Priority Data
Sep. 15, 2010 (DE) .......... 10 2010 040 822

(51) Int. Cl.
| | |
|---|---|
| C07D 233/54 | (2006.01) |
| C07D 233/60 | (2006.01) |
| C07D 233/61 | (2006.01) |
| C07D 233/06 | (2006.01) |
| C07F 13/00 | (2006.01) |
| C07F 15/06 | (2006.01) |
| A61K 49/00 | (2006.01) |
| C07F 1/08 | (2006.01) |
| C07F 11/00 | (2006.01) |
| C07F 15/00 | (2006.01) |
| C07F 15/02 | (2006.01) |
| C07F 15/04 | (2006.01) |
| G01N 33/50 | (2006.01) |
| G01N 33/68 | (2006.01) |

(52) U.S. Cl.
CPC .............. *C07D 233/06* (2013.01); *A61K 49/00* (2013.01); *C07D 233/60* (2013.01); *C07D 233/61* (2013.01); *C07F 1/08* (2013.01); *C07F 11/00* (2013.01); *C07F 13/00* (2013.01); *C07F 15/006* (2013.01); *C07F 15/0046* (2013.01); *C07F 15/02* (2013.01); *C07F 15/04* (2013.01); *C07F 15/06* (2013.01); *G01N 33/50* (2013.01); *G01N 33/68* (2013.01); *Y10T 436/143333* (2015.01); *Y10T 436/147777* (2015.01)

(58) Field of Classification Search
CPC .. C07D 233/00; C07D 233/06; C07D 233/54; C07D 233/60; C07D 233/61; C07D 293/00
USPC ............ 424/9.1, 9.6; 548/103, 109, 110, 112, 548/313.7, 335.1, 336.1
See application file for complete search history.

(56) References Cited

U.S. PATENT DOCUMENTS 5,874,587 A  2/1999 Donovan et al.

OTHER PUBLICATIONS

F. Ekkehardt Hajn et al. Heterocycli Carbenes: Synthesis and Coordination Chemistry, (Angew Chem. Int. Ed. 2008, 47, 3122-3172).*
Elena Mas-Marze et al. Carbene Complexes of Rhodium and Iridium from Tripodal N-Heterocyclic Carbene Ligands: Synthesis and Catalytic Properties, Inorg. Chem. 43(6), 2213-2219, 2004.*
International Search Report for PCT/EP2011/065266 dated Oct. 21, 2011.

\* cited by examiner

*Primary Examiner* — Michael G Hartley
*Assistant Examiner* — Jagadishwar Samala
(74) *Attorney, Agent, or Firm* — Marshall, Gerstein & Borun LLP

(57) ABSTRACT

The present invention relates to imidazolium salts, particularly imidazolium salts of the general formula I as well as the respective carbene metal complexes and their utilization as bioanalytical tags for biomolecules.

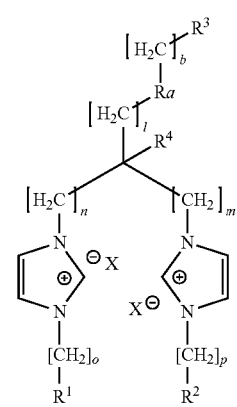

6 Claims, No Drawings

IMIDAZOLIUM SALTS AND CARBENE METAL COMPLEXES BASED THEREON FOR USE AS BIOANALYTICAL MARKERS FOR BIOMOLECULES

BACKGROUND OF THE INVENTION

1. Field of the Invention

The present invention relates to imidazolium salts, the respective carbene metal complexes as well as their utilisation in bioanalytical tags for biomolecules.

2. Related Technology

The research into the structure and functionality of biomolecules like proteins and carbohydrates as well as genomes and gene transcripts requires either special derivatives and/or mass spectrometric analysis. Methods used are for instance ESI (Electron Spray Ionization) [I], MALDI (Matrix-Assisted Laser Desorption Ionization) [2] and ICP-MS (Inductively Coupled Plasma-Mass Spectrometry) [3-5]. Such processes cause separation and purification steps by means of liquid chromatography (LC) or high performance liquid chromatography (HPLC) [6]. This requires techniques that are a combination of purification and analysis and are usually named by an acronym that combines the names of the individual techniques (hyphenated techniques).

The structure and the sequential architecture of the named biomolecules make great demands on the quantitative analysis. Particularly, the absence of quantitatively measurable functional groups and the limited availability of suitable heteroatoms respectively complicate the application of analytic methods like fluorescence spectroscopy or UV-vis spectroscopy as well as the use of electroanalytical methods. Even ICP-MS becomes more difficult or impossible [6] without an additional derivatisation step. Often, a so-called derivatisation step occurs, whereby a chromophoric, fluorophoric or electroactive group is incorporated into the analyte. The introduction of a heteroelement as respective derivatisation step enables access to ICP-MS studies [7].

For various medicinal-chemical applications, initial derivatisation steps were developed for the routine determination of certain analytes and were introduced into the respective protocols. The greatest disadvantage of this is the limitation to the simultaneous detection of only a single analyte. For the detection of more than one analyte, multiple detection sequences are necessary. The simultaneous detection is presently impossible. Protocols for the simultaneous detection of more than one analyte, preferably by applying identical analytical methods, are therefore urgently needed [8].

The simultaneous measurement of different analytes by means of tandem mass tags (TMT) or isobaric data recognition (isobaric tagging) for relative and absolute quantification (iTRAQ) [9,10] is possible in the field of proteomics. But, isobaric tagging techniques require marking with heavy isotopes ($^2$D, $^{13}$C, $^{15}$N) in an expensive, multistep synthesis, although the tags are commercially available.

Tagging methods should provide stable tags that allow a low detection limit and are non-toxic and inexpensive at the amounts used. Further, it should be possible to introduce them quantitatively and specifically. A broad range of individual tags should be available, which enables the simultaneous detection of different analytes.

Organometallic compounds or metal coordination compounds have the potential to fulfil all these demands. Several classes of compounds have already been synthesized and have found application as bioanalytical tags (BAT) [6]. In this sense "stable" means the compound is stable towards air and moisture and is usable for coordination compounds and for organometallic compounds. But "stable" also means stable with respect to leaching and in general towards displacement from the biomolecule. In the case of metal containing BATs, this means a strong coordination of the ligand(s) to the metal, which should be possible best by means of a combination of chelate ligands and N-heterocyclic carbenes (NHC) [11,12].

Promising classes of compounds that are usable for BAT applications are metal carbonyls, carbene complexes (Fischer and Wanzlick-Arduengo), as well as ferrocene and chelate complexes [6]. But, metal carbonyl complexes are susceptible to an early loss of carbonyl ligands in mass spectrometry, which complicates the analysis of spectra [13]. On the other hand, they offer a unique window of detection for IR-spectroscopy [14]. Ferrocenes are definitely the furthest developed class of compounds for electrochemical detection. But here, too, there are limitations with respect to derivatisation and thus multiple determination of analytes.

In total, not even ferrocenes can simultaneously combine the advantages of electrochemical detection, unique isotope patterns for MS-detection and a broad modification range.

DESCRIPTION OF THE INVENTION

Consequently, it is the object of the present invention to provide compounds that overcome the aforementioned disadvantages.

The object is solved by the imidazolium salts of the general formula I,

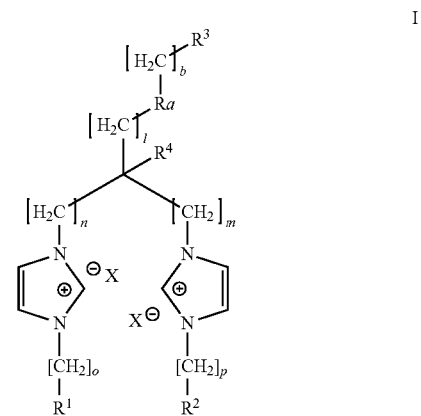

wherein b, I, m, n, o and p are the same or different and are each independent of each other zero or an integer number from 1 to 3; and X⁻ is an anion;

R is chosen from the group of $C_5$-$C_{15}$-aryl and $C_4$-$C_{14}$-hetaryl and a is zero or 1;

$R^1$ and $R^2$ are the same or different and open chained, branched or unbranched or are part of a ring or a ring system and are chosen from the group consisting of hydrogen, $C_1$-$C_{12}$-n-alkyl, $C_3$-$C_{12}$-branched alkyl, $C_3$-$C_{12}$-cycloalkyl, $C_2$-$C_{12}$-alkenyl, $C_7$-$C_{20}$-arylalkyl, $C_5$-$C_{14}$-aryl, which itself is either the same or differently substituted by one or more branched or unbranched $C_1$-$C_3$-alkyl groups, wherein the cyclic and aromatic systems are single rings or several condensed, annelated or isolated rings or form a ring system together with the imidazolium ring of the structure according to formula I;

$R^3$ is chosen from the group of —NH₂, —NCS, —NCO, —CHO, —CH(NH₂)(CH₃), —NHC(=O)CH₂-halogenide, —(CH$_2$)$_{1-3}$—SH, —B(OH)$_2$, -4(1,2,4-triazoline-3,5-dione); —COOH, —C(═O)R'; wherein R' is chosen from —OR" with R" chosen from C$_1$-C$_{12}$-alkyl and C$_5$-C$_{14}$-aryl; —NH—NH$_2$, —NH$_2$, —C$_0$-C$_1$-alkyl-halogenide, —OH, -piperazyl, -maleimidyl, —O—cyclopentadionyl, —(CH$_2$)$_{1-2}$—(NH)$_{0-1}$—(CH$_2$)$_{1-5}$—C(═O)—O-cyclopentadionyl, wherein the cyclopentadione ring can carry a —SO$_3$Na group and wherein the halogenides are preferably Cl, Br, I.

R$^4$ is hydrogen, R$^5$, wherein R$^5$ is the same or different from R$^1$ and R$^2$ and chosen from the same group as R$^1$, R$^2$ or an imidazolium ring of formula II,

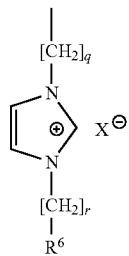

II wherein q and r are the same or different and each is independently of each other zero or an integer number from 1 to 3;
R$^6$ is the same or different to R$^1$ and R$^2$ and is chosen from the same group as R$^1$, R$^2$.

The anion X$^-$ is not subject to any limitations, i.e. it can be any anion that causes an overall neutral charge of the complex. Preferably named are halogenides like fluoride, chloride and bromide, but also other monoanions like nitrate, BF$_4^-$, BPh$_4^-$, PF$_6^-$, SbF$_6^-$ and Sb$_2$F$_{11}^-$, as well as doubly or triply charged anions like sulphates, phosphates.

For the group R', all groups are usable that are disclosed in Seiwart/Karst, Anal Bioanal Chem (2008), 390:181-200. In particular, this relates to the functional groups described in table 1 on pages 184-187, wherein the functional group begins with ferrocene (there called Fc). These functional groups are explicitly incorporated by reference.

Preferably, the groups R$^1$, R$^2$ and as the case may be R$^6$ are the same or different and chosen from the group of C$_1$-C$_6$-n-alkyl, preferably from the group of C$_1$-C$_3$-n-alkyl. R$^1$, R$^2$ and R$^6$, where applicable, are especially preferred methyl groups.

The indices b, l, m, n and q, where applicable, are preferably zero or 1, more preferred n, m and q, where applicable, are zero or 1 and b and l zero.

A preferred embodiment is characterized by o, p and r, where applicable, being zero. If o, p and r, where applicable, are zero, then the respective group R$^1$, R$^2$ and R$^6$, where applicable, are directly bonded to the imidazole ring.

A further variant is characterized by a being zero. In this case, the groups [(CH$_2$)]$_l$ and [(CH$_2$)]$_b$ are directly linked to each other. Together, the indices l and b stand for zero or for integer numbers from 1 to 6 (l+b=1 to 6), preferably the indices l and b together stand for at least 1 (l+b≥1).

The aromatic group R is chosen from C$_5$-C$_{15}$-aryl and C$_4$-C$_{14}$-heteroaryl, preferably from C$_5$-C$_7$-aryl and C$_4$-C$_6$-heteroaryl, more preferred R is a C$_6$-aryl group. If the aromatic group R is present, i.e. if a is 1, then [(CH$_2$)]$_l$ and [(CH$_2$)]$_b$ are in orto-, meta- or para-position with respect to the C$_6$-aryl group. The para-substitution is preferred.

The group R$^3$, which is the functional group for the later linking to the respective biomolecule, is preferably chosen from —NH$_2$, —COOH, —CONH$_2$ and —COOR"', wherein R"' is a C$_1$-C$_6$-n-alkyl group, preferably a methyl or an ethyl group.

Examples for especially preferred representatives for imidazolium salts are depicted in the following scheme 1a.

Scheme 1a

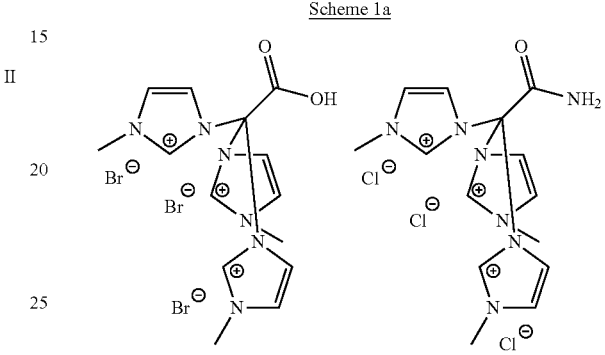

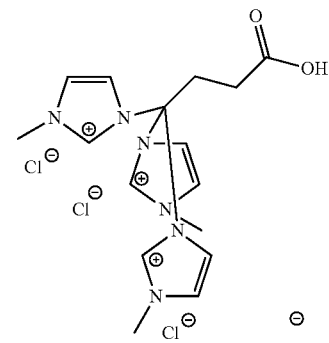

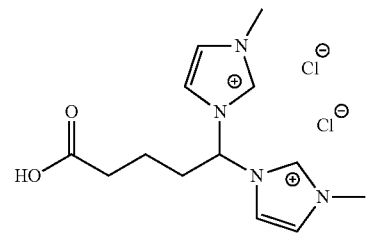

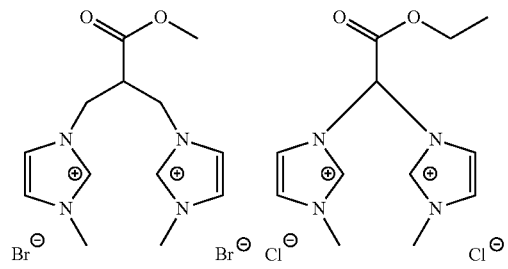

Another preferred representative is depicted in scheme 1b.

Scheme 1b

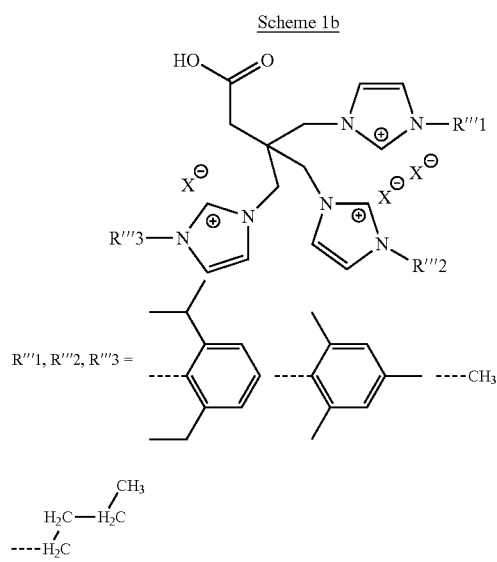

The groups R′″1, R′″2 and R′″3 according to scheme 1b are each the same or different and independently of each other chosen from 1-(2,6-di-isopropylphenyl), 1-(2,4,6-trimethylphenyl), methyl and n-butyl as shown in scheme 1b. The anion X⁻ is not subject to any limitations. Preferably, the groups R′″1, R′″2 and R′″3 are the same, i.e. especially preferred representatives of the imidazolium salts from scheme 1b are shown in scheme 1c, wherein X⁻ is preferably F⁻, Cl⁻ or Br⁻.

Scheme 1c

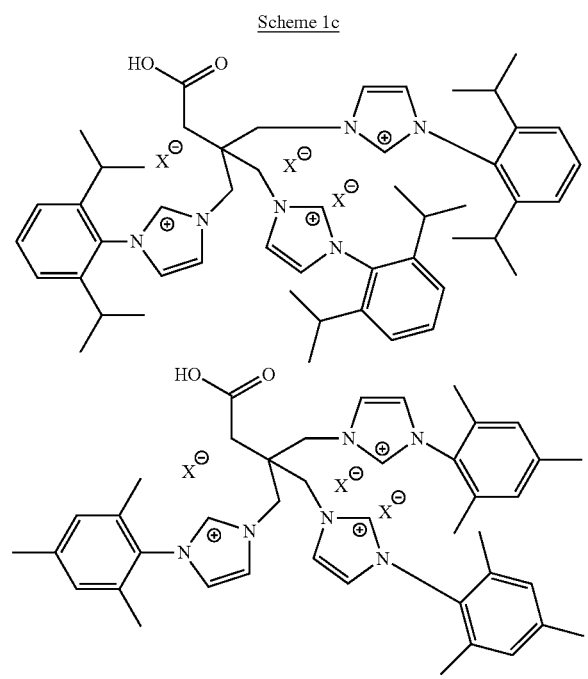

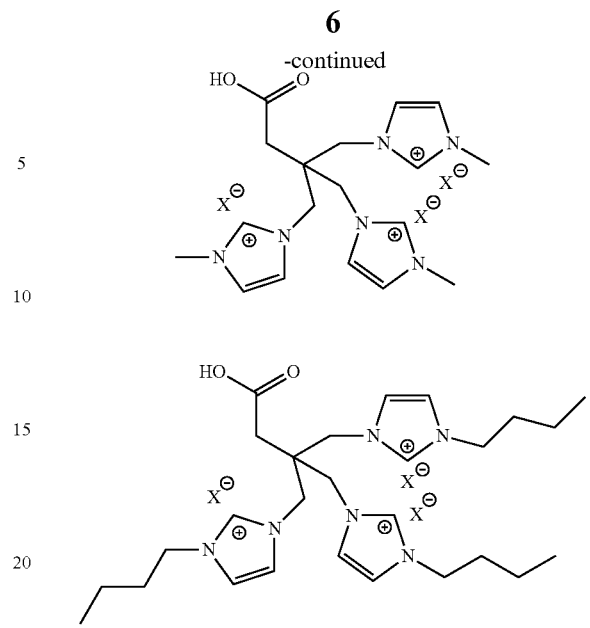

The combination of two functionalized bis-carbenes to a single tetrakis-carbene unit is likewise subject of the present invention. The basis for this are the imidazolium salts according to the general formula III, which in the following are called bridging imidazolium salts.

III

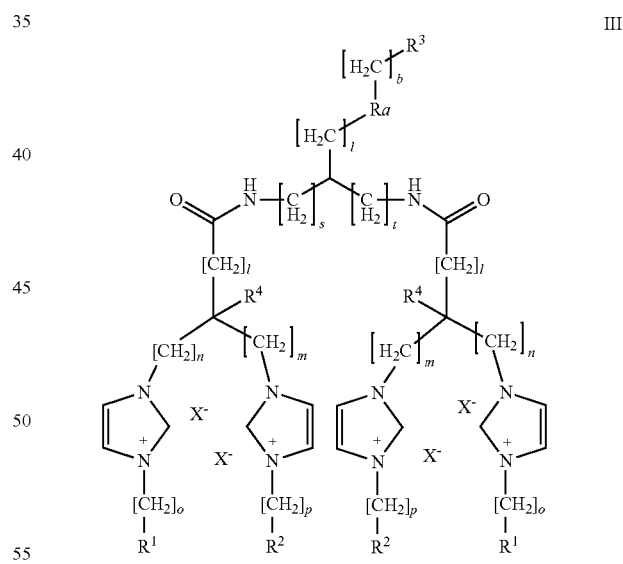

$R^1$ to $R^4$ and R as well as a, b, l, m, n, o and p have the same meaning at the bridging imidazolium salts as they were defined with respect to the imidazolium salts above. Further, the indices s and t are the same or different and independently of each other zero or an integer number from 1 to 3.

The synthesis of such bridging imidazolium salts is achieved preferably by coupling of two bidentate units by means of a [2+1] functional linker as it is exemplarily shown in scheme 2.

Scheme 2

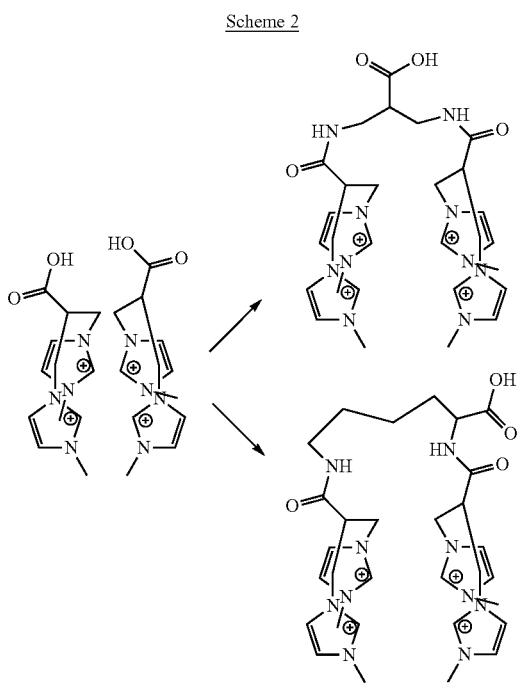

The imidazolium salts and bridging imidazolium salts according to the present invention are further reacted to N-heterocyclic carbene complexes.

Therefore, carbene metal complexes of the general formula IV are also subject of the present invention,

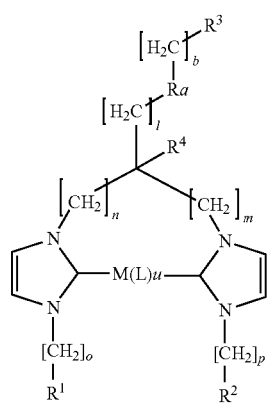

IV wherein $R^1$ to $R^4$ and R and optionally $R^6$ and a, b, l, m, n, o and p, where applicable, q and r, where applicable, have the meaning that was already defined with respect to the imidazolium salts and M is a metal of the main group elements or the transition metals (groups 3-12 of the Periodic Table of the Elements) including the lanthanides and the actinides, L is a ligand and u is an integer number from 1 to 4, wherein if u=2, 3 or 4, the ligands L are either the same or different and several ligands L, where applicable, form a bi- or polydentate chelate ligand and wherein if $R^4$=imidazole ring according to formula II, the imidazole ring also coordinates to the metal M.

Preferably, the metal M is chosen from the group of metals of the 6.-12. group of the Periodic Table of the Elements. More preferred, the metal M is chosen from the group of metals copper, iron, ruthenium, nickel and palladium or from the group of metals technetium, rhenium and cobalt.

The ligand L is chosen from the group

CO;

nitrile;

isonitrile;

nitrosyl;

halogenide ion;

hydrogen atom;

$C_1$-$C_{12}$-alkyl anion, allyl anion, methylallyl anion, benzyl anion, $C_6$-$C_{14}$-aryl anion, $C_1$-$C_{12}$-alkoxy anion, $C_6$-$C_{14}$-aryloxy anion, $C_1$-$C_{12}$-heteroalkyl anion, $C_6$-$C_{14}$-heteroaryl anion, $C_1$-$C_{12}$-heteroalkoxy anion, $C_6$-$C_{14}$-heteroaryloxy anion or $C_6$-$C_{14}$-heteroaryloxy anion, which is unsubstituted or the same or differently substituted by one or more $C_1$-$C_{12}$-alkyl groups or $C_1$-$C_{12}$-heteroalkyl groups, wherein the heteroatoms are chosen from the group B, Al, Ga, In, N, P, As, Sb, Bi, Si, Ge, Sn, Pb, O, S, Se and Te and wherein the anions are unsubstituted or wholly or partially substituted with one or more than one, same or different heteroatoms from the same group, in the form of functional groups, wherein the cyclic and aromatic systems are single rings or several annelated or isolated rings;

primary, secondary, tertiary amine;

primary, secondary, tertiary phosphane;

primary, secondary, tertiary phosphite or carbene.

The ligand L can be a chelate ligand. Preferably, the ligand L is chosen from the group of halogenide ions, particularly preferred are bromide or chloride.

The unit of transition metal and carbene enables the application in quantitative detection on the basis of IR, UV-vis, fluorescence spectroscopy, ICP-MS or on the basis of electrochemical methods or, where applicable, with the help of a radioactive indicator. It can be called a detection unit. The functional group $R^3$ enables the coupling of the detection unit to the respective biomolecule. By modifying the metal and/or the metal-coligand (ligand L), the detection method or the position of the detection signal can be varied. This means that the choice of detection method is put into the hands of the user and is no longer the limiting factor. The variation of the signal location within the detection method enables the simultaneous measurement of several BATs, i.e. the analysis of several analytes in one step becomes possible in this way.

As an example, scheme 3 shows a series of different but similar molybdenum carbonyl carbene complexes, whose A1 stretching vibration frequency in the IR spectrum varies depending on the denticity of the functionalized NHC-ligand [14].

Scheme 3

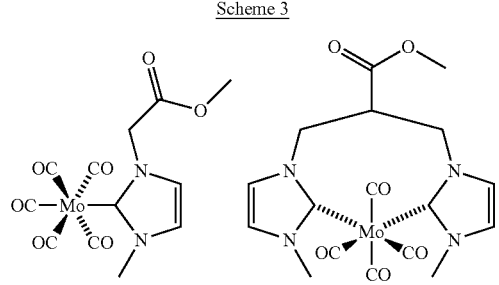

-continued

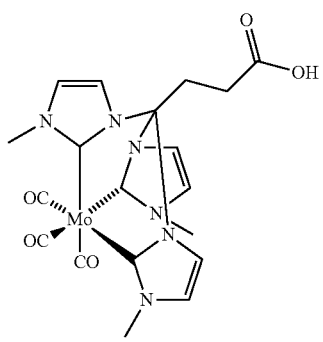

Ruthenium complexes are often used for electrochemical detection methods. In particular, the redox couple Ru(II)/Ru(III) can be used almost as generally as the redox couple Fe(II)/Fe(III) of the ferrocenes. The later can be varied only moderately by modifying the substituents at the cyclopentadienyl ring. This is synthetically difficult and limiting with respect to the actual shift of the signal. In contrast, the modification of the ruthenium NHC complexes of the present invention is facile. Scheme 4 gives an overview over the Fe and Ru complexes.

Scheme 4

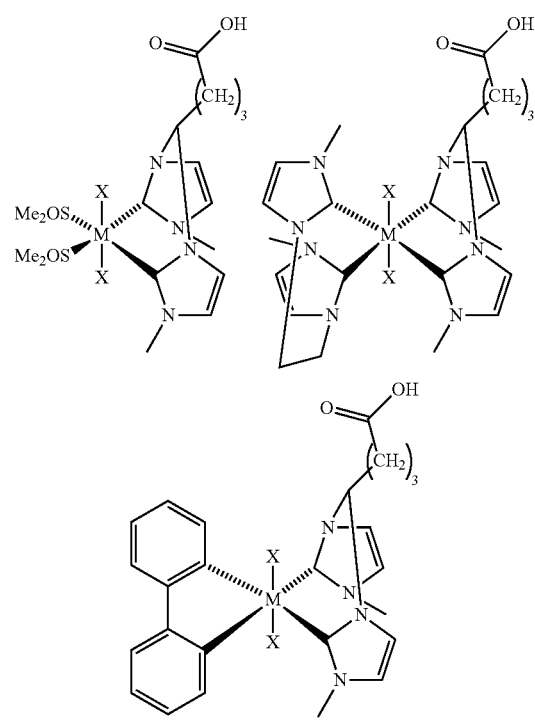

M = Ru, Fe
X = halogen

With respect to ICP-MS, a variation of the metal atom can be used to identify different analytes quantitatively. By using the different isotope patterns of the metal atoms, the simultaneous measurement of different analytes can be achieved solely by mass spectrometry. Scheme 5 shows several suitable carbene metal complexes.

Scheme 5

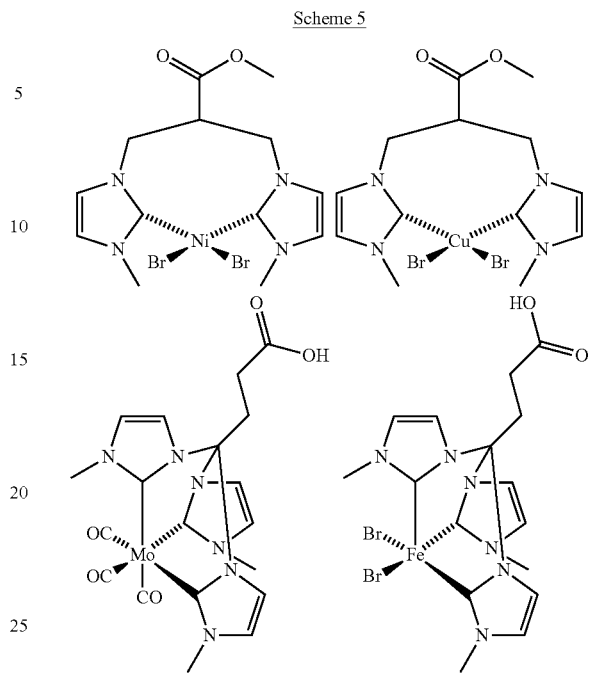

Particularly preferred carbon metal complexes (BATs) that are used according to the present invention, are shown in the following scheme 6.

Scheme 6

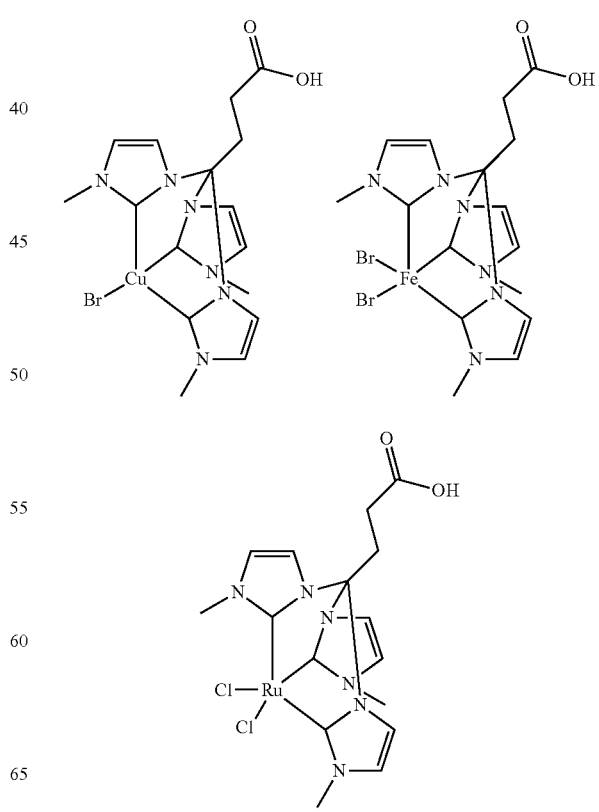

-continued

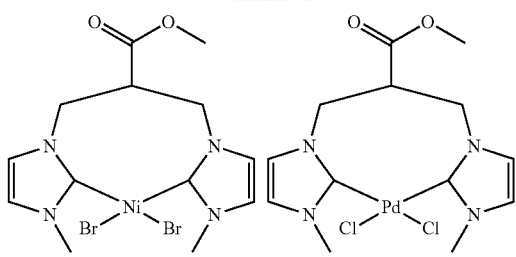

With reference to the above mentioned imidazolium salts of the general formula III, carbene metal complexes of the general formula V are also subject of the present invention,

V

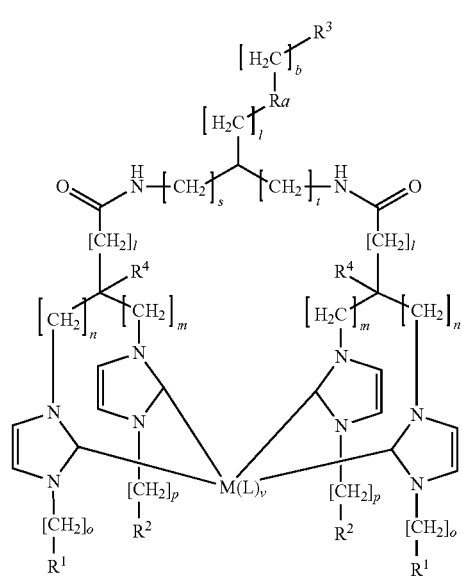

wherein $R^1$ to $R^3$ and R and a, b, l, m and n as well as M and L have the above mentioned meaning, $R^4$ is hydrogen and v is zero, 1 or 2. They are called bridged carbene metal complexes or combinatorial BATs, respectively. Because of the positive charge of the individual imidazolium rings, such combinatorial BATs are more difficult to synthesise. As one possible way for their synthesis, a sequential strategy is applied, wherein two bidentate units are connected to a tetradentate ligand via a [2+1] functional linker, as it is depicted in scheme 2 above. This grouping is subsequently reacted to the carbene metal complex. Scheme 7 offers an overview.

Scheme 7

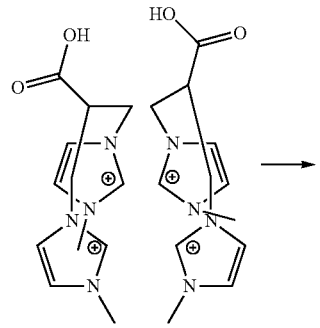

-continued

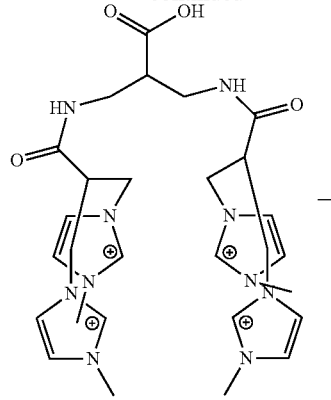

Within the scope of the invention, at first two bidentate ligands can be reacted to a tetrakis-carbene metal complex and then, the two units are linked to each other. Also, a functionalized and a non-functionalized bis-carbene unit can be used for the synthesis of these BAT.

In a carbene metal complex with a tetradentate ligand, as shown at the far right in scheme 7, the metal is hydrophobicly encapsulated. In this shape, transfer through hydrophobic barriers like cell membranes is possible. The carbene metal complexes, i.e. the simple as well as the bridging carbene metal complexes, are applied as bioanalytical tags for biomolecules, wherein the metal complexes are covalently bonded to a respective functional group of the biomolecule through the functional group of $R^3$, preferably a hydroxyl, thiol or amino group, particularly preferred through a thiol or amino group.

The biomolecule to be analyzed in each case originates from the group of proteins, peptides, carbohydrates, nuclein bases (cytosine, uracil, thymine, guanine, adenine, hypoxanthine), DNA and RNA as well as hybrides containing one or more members of this group.

By modifying the linker unit of the BAT, different functional groups of the biomolecule can be targeted. The linker unit is defined as the group $[CH_2]_l—R_a—[CH_2]_b—R^3$. Preferred targets according to the present invention are amino functionalities like in lysine or the N-terminus of peptides. For the latter, a N-succinimide ester can be used as linker. For the coupling with amines, carbonyl groups can be used as group $R^3$. Other targetable functional groups are thiol groups, e.g. in the cysteine side chains of peptides, wherein, for example, N-succinimide or iodacetamide are used as linker. For molybdenum complexes, some of the preferred carbene metal complexes with functional groups respectively with modified functional groups according to the present invention are shown as examples in schemes 8 and 9.

Scheme 8

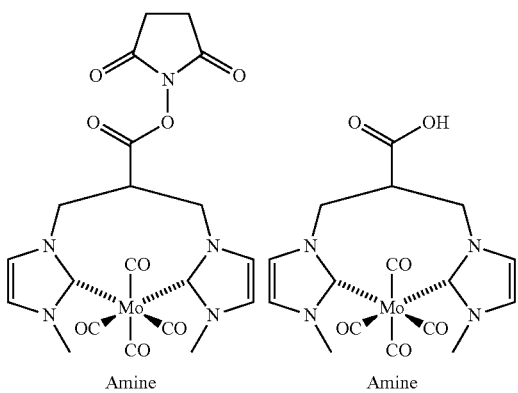

Scheme 9

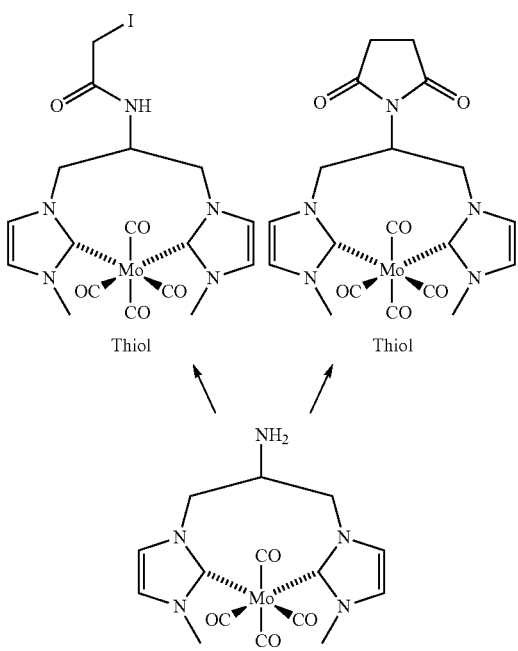

The bonding of the respective carbene metal complex can for instance be based on a carboxylic acid or an amine as functional group $R^3$. The carboxylic acid is reacted with N-succinimide. Subsequently, this is reacted with the thiol or the amino group of the respective biomolecule, which results in a thioether or an amide bond. An amino group as functional group $R^3$ can be reacted to iodoacetamide, which yields a thioether after reaction with a thiol group of a biomolecule. In the same way, the amino group ($R^3$) can be reacted with succinic acid or succinimide, which again yields a thioether or an amide bond after reaction with a thiol or amino group of the biomolecule, respectively. Preferably, the biomolecule is bonded covalently to the functional group $R^3$ through a thioether or an amide bond.

For the coupling to the biomolecule, a reverse synthetic strategy can be used, i.e. first the imidazolium salt is bonded to the biomolecule and subsequently the metal is introduced into the carbene precursor. In this way, a broad range of quasi "premarked" biomolecules can be generated, wherein the decision about the detection method can be deferred to the time, when the metal is selected. That makes the isolation, purification as well as handling easier, as the choice of detection method can be postponed to the point in time when the actual analysis is imminent.

The procedure via the normal way, i.e. the generation of the carbene metal complex and subsequent bonding to the biomolecule is also possible. Both ways can be followed. In the case of the transition metal carbonyl precursors, it is more promising, because of their sensitivity towards oxygen, to first generate the carbene metal complexes and to subsequently bond them fully coordinated to the biomolecule.

During the application of the carbene metal complexes for the analysis of biomolecules, the biomolecules are preferably analyzed as a whole or in parts. Particularly preferred are the carbene metal complexes, covalently bonded to a biomolecule, for the transport of metals, preferably technetium, rhenium or cobalt, to specific target organs (radio medicine). For the transport, the bis- and tris-, i.e. the simple carbene metal complexes as well as the tetrakis-systems, i.e. the bridging carbene metal complexes can be used.

Literature

[1] J. B. Fenn, M. Mann, C. K. Meng, S. F. Wong, C. M. Whitehouse, Science 246 (1989) 64

[2] L. A. Finney, T. V. O'Halloran, Science 300 (2003) 931.

[3] M. Wang, W. Y. Feng, Y. L. Zhao, Z. F. Chai, Mass Spectrom. Rev. 29 (2009) 326.

[4] J. Bettmer, N. Jakubowski, A. Prange, Anal. Bioanal. Chem. 386 (2006) 7.

[5] A. Sanz-Medel, Anal. Bioanal. Chem. 391 (2008) 885.

[6] S. Bomke, M. Sperling, U. Karst, Anal. Bioanal. Chem. (2010) doi: 10.107/s00216-010-3611-1

[7] J. Szounar, Analyst 130 (2005) 442.

[8] N. Metzler-Nolte, Angew. Chem. 113 (2001) 1072.

[9] C. J. Koehler, M. Strozynski, F. Kozielski, A. Treumann, B. Thiede, J. Proteome Res. 8 (2009) 4333.

[10] L. Dayon, A. Hainard, V. Liecker, N. Turck, K. Kuhn, D. F. Hochstrasser, P. R. Burkhard, J.-C. Sanchez, Anal. Chem. 80 (2008) 2921.

[11] F. E. Hahn, M. Jahnke, Angew. Chem. Int. Ed. 47 (2008) 3122.

[12] O. Kühl, Chem. Soc. Rev. 36 (2007) 592.

[13] a) C. J. Adams, M. I. Bruce, P. Duckworth, P. A. Humphrey, O. Kühl, E. R. T. Tiekink, W. R. Cullen, P. Braunstein, S. Coco Cea, B. W. Skelton, A. H. White; J. Organomet. Chem. 467, 1994, 251; b) C. J. Adams, M. I. Bruce, O. Kühl, B. W. Skelton, A. H. White; J. Organomet. Chem. 445, 1993, C6; c) O. Kühl, M.Sc. Thesis, Tübingen 1992.

[14] O. Kühl, Coord. Chem. Rev. 249, 2005, 693.

[15] B. Seiwert, U. Karst, Anal. Bioanal. Chem. 390 (2008) 181.

EXAMPLES

Example 1

3,3'-(2-(Methoxycarbonyl)propane-1,3-diyl)bis(1-methyl-imidazole-2-ylidene)dibromide N-Methylimidazole (1.15 g, 14 mmol) was dissolved in dioxane (15 mL) and methyl-3-bromo-2-(bromomethyl) propionate (1.82 g, 7 mmol) was added. The reaction mixture was heated to 60° C. for 6 h while being stirred. The solvent was partly removed under vacuum and a white powder obtained that was washed with hexane. Yield: 2.948 g; 99%.

$^1$H NMR (DMSO, ppm): δ: 3.63 (s, 3 H, OCH$_3$); 3.78 (quintett, $^3J_{HH}$=6.3 Hz, 1 H, CH); 3.88 (s, 6 H, NCH$_3$); 4.54 (dd, $^3J_{HH}$=6.5 Hz, $^3J_{HH}$=1.4 Hz, 4 H, CH$_2$); 7.75 (dd, $^3J_{HH}$=1.7 Hz, $^4J_{HH}$=1.7 Hz, 2 H, H$^5$); 7.79 (dd, $^3J_{HH}$=1.7 Hz, $^4J_{HH}$=1.7 Hz, 2 H, H$^4$); 9.21 ppm (s, 2 H, H$^2$)

$^{13}$C NMR (DMSO, ppm): δ: 35.95 (NCH$_3$); 45.34 (CH$_2$); 47.13 (OCH$_3$); 52.72 (CH); 122.70 (C$^5$); 123.79 (C$^4$); 137.41 (C$^2$); 169.95 (C=O).

Elemental analysis: Calculated for $C_{13}H_{20}Br_2N_4O_2$ (424.37 g·mol$^{-1}$): C, 36.79; H, 4.75; N, 13.26. found: C, 36.70; 5.29 H, 13.30; N.

Example 2

3,3'-(2-(Methoxycarbonyl)propane-1,3-diyl)bis(1-(2, 4,6-trimethylphenyl)-imidazole-2-yliden)dibromide 2,4,6-Trimethyl-N-imidazole (0.996 g, 5.35 mmol) and methyl-3-bromo-2-(bromomethyl)propionate (0.695 g, 2.67 mmol) were dissolved in 15 ml dioxane and heated to 70° C. for 8 h while stirring. The solvent was removed under vacuum and a highly viscous dark yellow oil obtained. Quantitative yield.

$^1$H NMR (DMSO, ppm): δ=2.00 (s, 6 H, o-CH$_3$); 2.01 (s, 6 H, o-CH$_3$); 2.33 (s, 6 H, p-CH$_3$); 3.71 (s, 3 H, OCH$_3$); 7.15 (s, 4 H, Ar—H); 7.92 (dd, $^3J_{HH}$=1.7 Hz, $^4J_{HH}$=1.6 Hz, 1 H, H$^5$); 7.96 (dd, $^3J_{HH}$=1.8 Hz, $^4J_{HH}$=1.7 Hz, 1 H, H$^5$); 8.00 (dd, $^3J_{HH}$=1.6 Hz, $^4J_{HH}$=1.7 Hz, 1 H, H$^4$); 8.04 (dd, $^3J_{HH}$=1.8 Hz, $^4J_{HH}$=1.7 Hz, 1 H, H$^4$); 9.37 (dd, $^4J_{HH}$=1.7 Hz, $^4J_{HH}$=1.5 Hz, 1 H, H$^2$); 9.55 (dd, $^4J_{HH}$=1.5 Hz, $^4J_{HH}$=1.3 Hz, 1 H, H$^2$)

$^{13}$C NMR (DMSO, ppm): δ: 16.82 ( ); 16.87 ( ); 20.58 ( ); 30.69 ( ); 44.81 ( ); 49.75 ( ) 52.33 ( ); 120.75 ( ); 123.19 ( ); 123.45 ( ) 124.09 ( ); 129.18 ( ) 129.24 ( ); 131.10 ( ); 131.26 ( ); 132.09 ( ); 133.46 ( ); 134.25 ( ); 134.34 ( ); 135.55 ( ); 138.17 ( ); 140.09 ( ); 140.29 ( ); 164.82 (C=O)

Example 3

2,2,2-Tris-N-Methylimidazole-acetic acid (Tris-COOH)

2.0 g Tribromo acetic acid (6.73 mmol) were stirred overnight in a round bottom flask together with 1.6 ml N-methylimidazole (20.20 mmol) in 20 ml THF and subsequently the solvent was removed under vacuum. Quantitative yield of an ionic liquid.

$^1$H NMR (DMSO, ppm): δ: 3.64 (s, 9 H, CH$_3$), 6.87 (s, 3 H, H$^5$), 7.09 (s, 3 H, H$^4$), 7.55 (s, 3 H, H$^2$), 7.70 (s, 1 H, COOH)

$^{13}$C NMR (DMSO, ppm): δ: 32.73 (CH$_3$), 120.45 (C$^5$), 128.36 (C$^4$), 137.86 (C$^2$), quarternary carbon atoms not detected.

Example 4

2,2,2-Tris-N-Methylimidazole-acetic acid amide (Tris-CONH$_2$)

4.875 g (30 mmol) 2,2,2-Trichloroacetamide were dissolved in 40 ml THF and 7.2 ml (90 mmol) N-methylimidazole added under stirring. Stirring was continued overnight and then the solvent removed under vacuum. Yield: 12.03 g; 98%.

$^1$H NMR (DMSO, ppm): δ: 3.63 (s, 9 H, CH$_3$), 6.89 (s, 3 H, H$^5$), 7.09 (s, 3 H, H$^4$), 7.56 (s, 3 H, H$^2$), 8.46 (s, 1 H, NH$_2$), 8.59 (s, 1 H, NH$_2$)

$^{13}$C NMR (DMSO, ppm): δ: 32.77 (CH$_3$), 93.20 (C), 120.52 (C$^5$), 128.41 (C$^4$), 137.92 (C$^2$), 163.09 (C=O)

Example 5

2,2-Bis-N-Metylimidazole-acetic acid ethylester (Bis-CO$_2$Et)

4.71 g Dichloro acetic acid ethylester (30 mmol) together with 4.8 ml N-methylimidazole (60 mmol) were stirred in 20 ml THF overnight in a round bottom flask and subsequently the solvent was removed under vacuum. Quantitative yield of an ionic liquid.

$^1$H NMR (DMSO, ppm): δ: 1.25 (t, $^3J_{HH}$=7.1 Hz, 3 H, CH$_3$), 3.64 (s, 6 H, NCH$_3$), 4.28 (qt, $^3J_{HH}$=7.1 Hz, 2 H, CH$_2$), 6.88 (s, 1 H, CH), 6.89 (s, 2 H, H$^5$), 7.11 (s, 2 H, H$^4$), 7.59 (s, 2 H, H$^2$)

$^{13}$C NMR (DMSO, ppm): δ: 13.67 (CH$_3$), 32.79 (NCH$_3$), 63.47 (CH), 64.99 (CH$_2$), 120.50 (C$^5$), 128.12 (C$^4$), 137.80 (C$^2$), 164.49 (C=O)

Example 6

Ru(tris-COOH)(SOMe$_2$)Br$_2$ 287 mg Tris-COOH (0.545 mmol) were reacted with 379 mg (1.64 mmol) Ag$_2$O in 20 ml CH$_2$Cl$_2$. Subsequently, 264 mg (0.545 mmol) [RuCl$_2$(DMSO)$_4$] were added and stirred overnight. The green fluid that was obtained, was filtered from the AgBr and concentrated under vacuum. After addition of hexane, a green, air stable compound precipitated that is soluble in water. It was purified with THF.

Yield: 239 mg (0.374 mmol; 69%) [RuBr$_2$(DMSO)(Tris-COOH)].

MS (MALDI-tof): 642.359 [M+] (isotopes at 638.360; 640.351; 642.359; 644.359; 646.350; 648.363), 598.402 [M+-CO$_2$], 517.600 [M+-CO$_2$-$^{81}$Br]

IR [cm$^{-1}$]: 1954.36 (C=O).

Elemental analysis for $C_{16}H_{22}Br_2N_6O_3RuS$ (638.68): calculated C, 30.09%; H, 3.47%; N, 13.22%. found C, 29.52%; H, 3.50%; N, 12.67%.

Example 7

Mo(Bis-CO$_2$Et)(CO)$_4$ 328.1 mg (1.02 mmol) Bis-CO$_2$Et were dissolved in 20 ml THF. 696.5 mg (3 mmol) Ag$_2$O were added. The suspension was stirred overnight in the absence of light. 296 mg (1.02 mmol) [Mo(CO)$_4$(NCMe$_3$)$_2$] were added and stirred overnight. After filtration, the volume was concentrated under vacuum. At −20° C. colorless crystals were obtained.

Yield: 191 mg (41%)

Example 8

Mo(Tris-CONH$_2$)(CO)$_3$ 409 mg (1 mmol) Tris-CONH$_2$ were dissolved in 20 ml CH$_2$Cl$_2$ and 367 mg (1.5 mmol) Ag$_2$O were added. The suspension was stirred overnight in the dark and subsequently, 290 mg (1 mmol) [Mo(CO)$_4$(NCCH$_3$)$_2$] were added. After stirring overnight, the suspension was filtered and the volume of the filtrate was concentrated under vacuum. At −20° C. colorless crystals were obtained.

Yield: 269 mg (47%).

Example 9

ω,ω,ω-Tris-(N-methylimidazolyl)-butanoic acid (0.25 THF)

994 mg (5.2 mmol) ω,ω,ω-Trichlor-butanoic acid and 1.24 ml (15.6 mmol) N-methylimidazole are stirred for 15 h in 25 ml THF. The solvent is removed under vacuum. The product remains as a colorless ionic liquid. It contains 0.25 molecules of THF per formula unit.

Yield: 2.4 g $^1$H NMR (DMSO-d6, ppm): δ: 2.65 (m, 2H, β-CH$_2$), 3.04 (m, 2H, α-CH$_2$), 3.64 (s, 9H, CH$_3$), 6.88 (s, 3H, H$^4$), 7.10 (s, 3H, H$^5$), 7.57 (s, 3H, H$^2$).

$^{13}$C NMR (DMSO-d6, ppm): δ: 31.29 (C-β), 32.78 (CH$_3$), 49.54 (C-α), 99.43 (C), 120.50 (C$^4$), 128.22 (C$^5$), 137.84 (C$^2$), 172.08 (C=O).

Example 10

ω,ω-Bis-(N-methylimidazolyl)-pentanoic acid 2 g (11.7 mmol) ω,ω-Dichloropentanoic acid and 1.85 ml (23.4 mmol) N-methylimidazole are stirred for 15 h in 30 ml THF. The solvent is removed under vacuum. The product remains as a colorless ionic liquid.

Yield: 3.9 g $^1$H NMR (DMSO-d6, ppm): δ: 1.68 (p, 2H, $^3J_{HH}$=7.4 Hz, β-CH$_2$), 2.18 (m, 2H, γ-CH$_2$), 2.30 (t, 2H, $^3J_{HH}$=7.4 Hz, α-CH$_2$), 3.64 (s, 6H, CH$_3$), 6.34 (t, 1H, $^3J_{HH}$=5.9 Hz, CH), 6.89 (s, 2H, H$^4$), 7.10 (d, 2H, $^3J_{HH}$=1.0 Hz, H$^5$), 7.59 (s, 2H, H$^2$).

$^{13}$C NMR (DMSO-d6, ppm): δ: 20.95 (C-β), 32.26 (C-γ), 32.79 (CH$_3$), 42.14 (C-α), 74.52 (CH), 120.51 (C$^4$), 128.09 (C$^5$), 137.79 (C$^2$), 174.02 (C=O).

Example 11

Fe(ω,ω,ω-Tris-(N-methylimidazolyliden)-butanoic acid)-(PPh$_3$)Br$_2$ 623 mg (1.42 mmol) ω,ω,ω-Tris-(N-methylimidazolyl)-butanoic acid and 598 mg (2.58 mmol) Ag$_2$O were stirred for 16 h in 30 ml dichloro methane. Then, 750 mg (1.42 mmol) [Fe(DMSO)$_4$Br$_2$] and 372 mg (1.42 mmol) PPh$_3$ were added. The suspension was filtered after 6 h, the filtrate concentrated under vacuum and hexane added. A reddish precipitate formed that was isolated and dried. Yield: 1.04 g (1.28 mmol, 90%).

MS (MALDI-tof) 808 [M+]

$^{31}$P NMR (DMSO-d6, ppm): δ: 7.88

The invention claimed is:

1. Imidazolium salts of the general formula I,

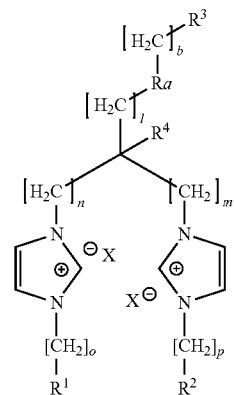

I wherein b, l, m, n, and q, where applicable, are the same or different and each is independent of each other and zero or 1, and o, p, and r, where applicable, are zero; and
X$^-$ is an anion;
a is zero or 1;
R is chosen from the group consisting of C$_5$-C$_{15}$-aryl and C$_4$-C$_{14}$-heteroaryl when a is 1;
R$^1$ and R$^2$ are the same or different and open chained, branched, or unbranched or are part of a ring or a ring system and are chosen from the group consisting of hydrogen, C$_1$-C$_{12}$-n-alkyl, C$_3$-C$_{12}$-branched alkyl, C$_3$-C$_{12}$-cycloalkyl, C$_2$-C$_{12}$-alkenyl, C$_7$-C$_{20}$-arylalkyl, and C$_5$-C$_{14}$-aryl, which itself is either the same or differently substituted by one or more branched or unbranched C$_1$-C$_3$-alkyl groups, wherein the cyclic and aromatic systems are single rings or several condensed, annelated, or isolated rings or form a ring system together with the imidazolium ring of the structure according to formula I;
R$^3$ is chosen from the group consisting of —NH$_2$, —COOH, —CONH$_2$, and —COOR", wherein R" is C$_1$-C$_6$-n-alkyl; and
R$^4$ is hydrogen or R$^5$, wherein R$^5$ is an imidazolium ring of formula II,

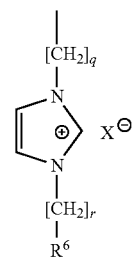

II wherein q is zero or 1 and r is zero, and R$^6$ is the same or different to R$^1$ and R$^2$ and chosen from the same group as R$^1$ and R$^2$.

2. Imidazolium salts according to claim 1, wherein the groups R$^1$, R$^2$, and R$^6$, where applicable, are the same or different and chosen from the group of C$_1$-C$_6$-n-alkyl groups.

3. Imidazolium salts according to claim 1, wherein n, m, and q, where applicable, are zero or 1 and b and l are zero.

4. Imidazolium salts according to claim 1, wherein $R^3$ is —COOR" and R" is a $C_1$-$C_6$-n-alkyl group.

5. A method for forming a bioanalytically tagged biomolecule, the method comprising:
   reacting an imidazolium salt according to claim 1 with a metal precursor to form a carbene metal complex; and
   reacting the carbene metal complex with a biomoelcule to form a bioanalytically tagged biomolecule comprising the carbene metal complex and the biomoelcule covalently bonded through a reaction product of the functional group $R^3$ and a respective functional group of the biomolecule.

6. A method for forming a bioanalytically tagged biomolecule, the method comprising:
   reacting an imidazolium salt according to claim 1 with a biomoelcule to form a bioanalytically pre-marked biomolecule comprising the imidazolium salt and the biomoelcule covalently bonded through a reaction product of the functional group $R^3$ and a respective functional group of the biomolecule; and
   reacting the bioanalytically pre-marked biomolecule with a metal precursor to form a bioanalytically tagged biomolecule comprising a carbene metal complex.

\* \* \* \* \*

UNITED STATES PATENT AND TRADEMARK OFFICE
CERTIFICATE OF CORRECTION

Page 1 of 1

PATENT NO.           : 9,150,515 B2
APPLICATION NO.      : 13/821941
DATED                : October 6, 2015
INVENTOR(S)          : Olaf Kuehl It is certified that error appears in the above-identified patent and that said Letters Patent is hereby corrected as shown below:

In the Claims:

At Column 19, line 7, "biomoelcule" should be -- biomolecule --.

At Column 19, line 9, "biomoelcule" should be -- biomolecule --.

At Column 19, line 16, "biomoelcule" should be -- biomolecule --.

At Column 19, lines 17-18, "biomoelcule" should be -- biomolecule --.

Signed and Sealed this
Seventh Day of June, 2016

Michelle K. Lee
*Director of the United States Patent and Trademark Office*